(12) United States Patent
Olson

(10) Patent No.: US 7,074,230 B2
(45) Date of Patent: Jul. 11, 2006

(54) EAR CLEANING DEVICE

(76) Inventor: Richard C. Olson, 28965 Lemon Rd., Mundelein, IL (US) 60060

( * ) Notice: Subject to any disclaimer, the term of this patent is extended or adjusted under 35 U.S.C. 154(b) by 246 days.

(21) Appl. No.: 10/369,915

(22) Filed: Feb. 20, 2003

(65) Prior Publication Data

US 2003/0187469 A1    Oct. 2, 2003

Related U.S. Application Data

(60) Provisional application No. 60/357,816, filed on Feb. 21, 2002.

(51) Int. Cl.
*A61F 9/00* (2006.01)
(52) U.S. Cl. .................................................... 606/162
(58) Field of Classification Search ................ 606/162; D24/147
See application file for complete search history.

(56) References Cited

U.S. PATENT DOCUMENTS

| | | | |
|---|---|---|---|
| 147,660 A * | 2/1874 | Leiner | ........................ 606/162 |
| 651,395 A | 6/1900 | Stapp | |
| 3,099,263 A | 7/1963 | Palazzolo | |
| 3,203,418 A | 8/1965 | Johnston | |
| 5,334,212 A | 8/1994 | Karell | |
| 5,374,276 A | 12/1994 | Lay | |
| 5,509,921 A | 4/1996 | Karell | |
| 5,632,756 A | 5/1997 | Kruglick | |
| 5,715,850 A | 2/1998 | Markgraaf | |
| 5,888,199 A | 3/1999 | Karell et al. | |
| D414,866 S * | 10/1999 | Szabo | ........................ D24/147 |
| 2001/0001828 A1 | 5/2001 | Begun | |

* cited by examiner

*Primary Examiner*—(Jackie) Tan-Uyen T. Ho
(74) *Attorney, Agent, or Firm*—Fitch, Even, Tabin & Flannery

(57) ABSTRACT

A disposable ear cleaning device having a one-piece, plastic body with an integral scoop at one end having a bowl portion having a smooth lower surface on the bowl. Openings may be formed in the bottom of the bowl for scraping wax and debris from the ear. The preferred openings are parallel slots. The preferred bowl has rounded, upper edges at the rim for scraping ear wax with the front, distal end at a lower height than a rear end of the bowl which is joined to a handle. The preferred handle may be fluted for gripping and turning the bowl when scraping ear wax. A flexible neck may join the bowl to the handle. A cotton swab may be provided at the end of the device opposite the bowl. The referred cleaning device weighs less than one gram and is inexpensive.

10 Claims, 2 Drawing Sheets

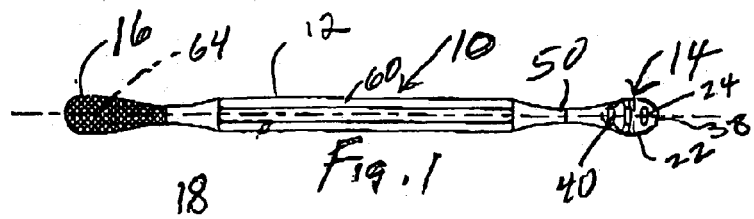
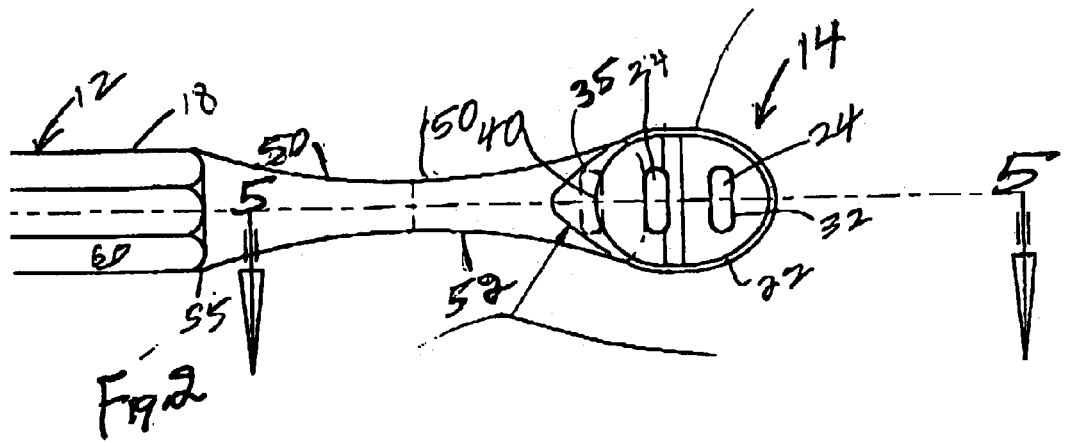
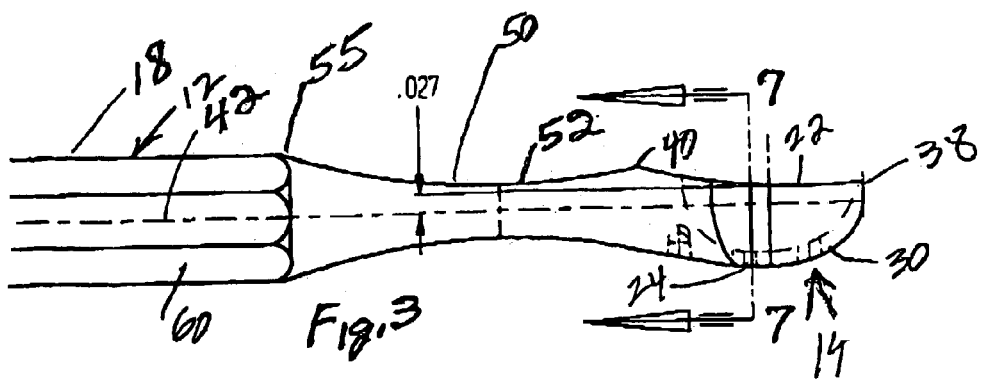

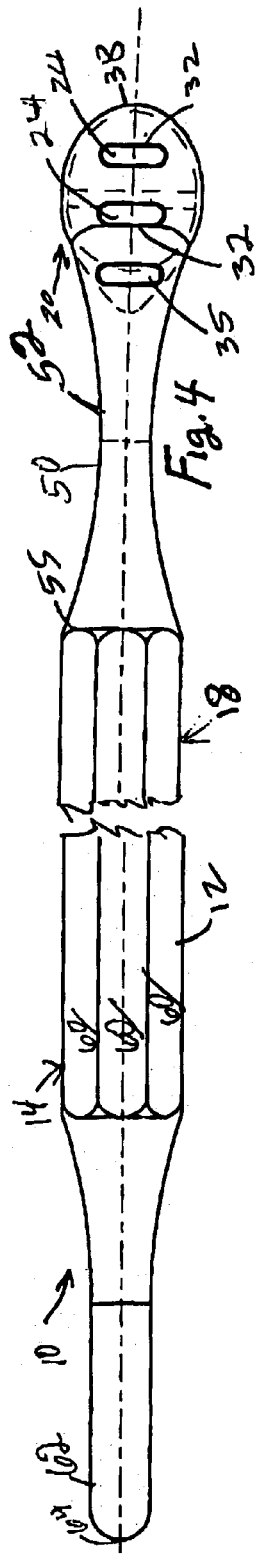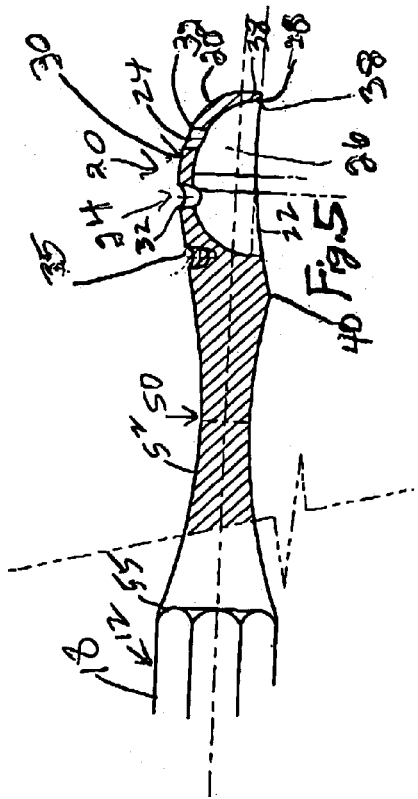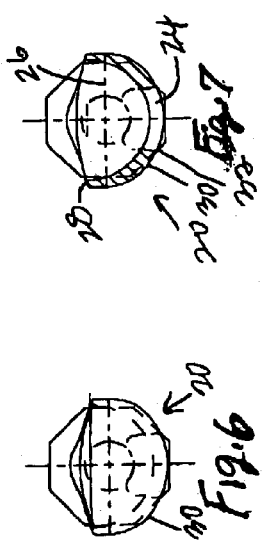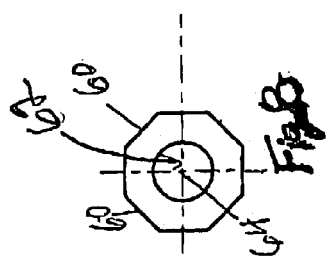

EAR CLEANING DEVICE

This application claims the benefit of U.S. Provisional Application No. 60/357,816; Filed Feb. 21, 2002.

FIELD OF THE INVENTION

This invention relates to a personal, disposable, ear cleaning device which is capable of being used by a person to effectively clean his or her own ears.

BACKGROUND OF THE INVENTION

The most commonly used ear canal hygiene method in use today is a cotton swab which in general works well to remove water and some particulates from the ear but is limited in its design at removing ear wax and excess ear debris. Ear wax and ear debris is actually smeared than removed and may even become more compacted making it more difficult to remove at a later time. The problem with cotton swabs in trying to remove ear wax is that it may actually push the wax deeper into the ear without removing the wax from the surface of the ear.

Various proposals for an ear cleaning device have been made but none of them appear to be commercially available to the consumer except for the one device that is non-disposable and sells for an expensive price, for example, about $5.00 and includes a depth stopper which limits the depth of insertion and has an outer loop or curette with sharp edges to scrape the wax from the ear. This stopper type of ear cleaning device having a curette is shown in U.S. Pat. Nos. 5,509,921; 5,888,199; 5,334,212; and 5,715,850. The problem with such a permanent, expensive ear cleaning device is that it needs to be cleaned and there is always a danger ineffective cleaning and subsequent cutting and a consequent infection. Additionally, the consumers are accustomed to having inexpensive, disposable instruments for which they pay a small price, rather than an expensive implement for cleaning their ears, which, in turn, has to be cleaned.

U.S. Pat. No. 5,374,276 discloses the use of a cotton swab for cleaning the auditory canal and the cotton swab is removed and discarded from the ear cleaning device which is intended to be reused. The consumer is expected to wrap and secure a cotton swab around the spiral hatch pattern on the one end of the handle portion of the ear wax remover. An extraction head on this ear wax remover comprises three similarly shaped projections extending radially outward from a shank. Each projection has the shape of a frustum of a cone. That is, the extraction head comprises three frustum cone shapes portions on the tip of the device. Thus, the ear wax remover tool is to be used over and over again with subsequent swab attachments after each usage.

Thus there is a need for a new and improved ear wax cleaning device, which is small, light-weight, readily disposable and has a more effective ear wax cleaning head, which is not in the form of a curette, but which is made with smooth edges and has an effective ear wax and debris collecting portion.

SUMMARY OF THE INVENTION

In accordance with the preferred embodiment, there is provided a new and improved one-piece, disposable ear cleaning device that effectively removes and collects excess wax and debris from the ear canal area to insure healthy and clean ear hygiene. This is achieved by a one-piece, disposable ear cleaning device of relatively light-weight and which is formed with a spoon or bowl-shaped scoop having rounded edges for cleaning the ear. One embodiment has openings with edges on the outer surface of the bowl for also collecting ear wax or debris. With fingertip control the user can operate the handle portion of the ear cleaning device to use either the edges about the rounded edges of the scoop or to use the back bowl surface openings to gently scrape or remove the debris from the ear and ear canal. Thus there is a dual manner of collecting ear wax and debris and there is provided a very smooth bowl surface for sliding along the ear canal without cutting the ear as the collecting edges scrape and remove the debris.

In the preferred embodiment, the outer edge front, distal of the bowl is lower than the inner rear edge of the bowl to provide a downward slope to the rounded side edges on the top of the bowl for scraping ear wax into the interior of the bowl. Preferably the ear cleaning device has the bowl attached by a flexible neck portion to the handle so that the bowl may flex and conform to the ear canal without scraping or damaging the same as the bowl slides along the surface of the ear.

In accordance with one embodiment, the ear cleaning device is provided with a cotton swab on an end of the handle opposite the bowl. The cotton swab is used to assist in any additional cleanup after use of the bowl and also could be used as an applicator for an ear cleaning solution. In this one embodiment, the cotton swab is not to be reused and is disposable along with the ear cleaning device which is made of a very small amount of plastic, for example, several devices to an ounce so that the entire ear cleaning device may be disposed of quickly.

By way of illustration only, the illustrated ear cleaning device is only about 3¼ inches in length and is only about 3/16 inch in width at the handle and that the bulbous end portion having the bowl-shaped scoop. Also, in this illustrated and preferred embodiment the openings on the bottom side of the smooth bowl comprise a pair of parallel openings or slots extending into the interior of the bowl and through which slots the ear collected ear wax or debris may pass for collection. A third, closed slot may also be provided inward of the parallel open slots for debris removal.

BRIEF DESCRIPTION OF THE DRAWINGS

The illustrated embodiment is shown in the attached drawings in which:

FIG. 1 is a perspective view of a ear cleaning device constructed in accordance with one embodiment of the invention;

FIG. 2 is an enlarged plan view of the ear cleaning device of FIG. 1;

FIG. 3 is an enlarged side-elevational view of the ear cleaning device of FIG. 1;

FIG. 4 is a bottom view of the ear cleaning device of FIG. 1;

FIG. 5 is a cross-sectional view taken along the line 5—5 of FIG. 2;

FIG. 6 is an end elevational view of the ear cleaning device of FIG. 3;

FIG. 7 is a cross-sectional view taken substantially along the line 7—7 of FIG. 3; and FIG. 8 is an opposite end view of the ear cleaning device from that of FIG. 3.

DETAILED DESCRIPTION OF THE PREFERRED EMBODIMENT

As shown in the drawings for purposes of illustration, the illustrated ear cleaning device 10 comprises a main plastic body portion 12 having a bowl or spoon 14 and in this embodiment shown in FIG. 1 having a cotton swab 16 at the opposite end of a handle portion 18 which extends between the bowl or spoon 14 and the cotton swab 16.

In accordance with the illustrated embodiment of the invention as best seen in FIGS. 2 and 5, the bowl 14 includes a rounded bowl or bulbous-shaped portion 20 that is integral with the body portion 12 of the ear cleaning device and has smooth rounded outer, upper side, edges 22 and ear cleaning openings 24 in the bowl portion for scraping and collecting ear wax or ear debris within a hollow interior 26 of the bowl. As best seen in FIG. 5, the edges 22 have a rounded radius 28 so that they will not scrape the ear with a sharp edge when collecting ear wax. Likewise the rear surface 30 of the bulbous portion having the openings 24 is also smooth and has rounded edges defining a slot or opening projecting inwardly into the hollow interior 26. The tool bowl is smooth to slide along the ear with the backside surface 30 of the bowl smoothly sliding along the ear and any wax will be caught by an edge 32 of an opening 24 to scrape and remove the ear wax will then pass through the opening 24.

In the illustrated embodiment of the invention, there are a pair of parallel openings 24 in the form of parallel slots as best seen in FIGS. 2 and 5. In addition, it is preferred that there is a third closed slot 35 which can also collect or scrape ear wax as the tool is being pulled backwardly in the ear. The third slot is optional. Manifestly, the number of openings 24, 35 and the size and shape of the openings may be varied from the illustrated embodiment having the parallel slots which seem to work quite well when using this smooth the rounded outer bowl portion to collect wax rather than the rounded top side edges 22 at the top of the bowl.

Also in accordance with the invention, as best seen in FIGS. 3 and 5, it is preferred to have the front tip or distal end 38 of the bowl be at a lower height than the rearward end 40 of the bowl as shown in FIGS. 3 and 5. By way of example only, the height or distance of the forward edge 38 from the axis center line 42 of the ear cleaning tool is in this instance is about 0.031 whereas the opposite highest point at the inner rear end 40, the scoop or bowl is about 0.060. Also, by way of example only, the top curved surface of the bowl is curved along a upward and rearwardly radius portion that is at a radius of 0.908 inch.

In accordance with another aspect of the illustrated embodiment, the handle portion 18 is joined to the bowl 14 by a flexible neck portion 50 on the body 12. Herein the portion is made with a reduced cross-sectional thickness. By way of example only, the neck portion at its smallest cross-section is less than one-half of the cross-sectional thickness of the handle. Herein the cross-sectional thickness of the neck is also curved along curved surfaces 52 as shown in FIGS. 2, 3, 4 and 5. The neck is curved on the opposite sides to gradually reduce the cross-sectional thickness between a junction point 55 with the handle and the upper rear end 40 of the bowl.

To provide a good gripping surface in order to be able to rotate the ear cleaning device without slipping, it is preferred to provide elongated flutes 60, herein there are eight flutes on the handle. The flutes are elongated, flat surfaces on the outer surface of the handle. Obviously, the shape of the flutes and the number of flutes can be different from that described herein. The cotton swab 16 is preferably with a bulbous-shape as shown in FIG. 1 and is attached to a cylindrical end 62 on the end of the handle opposite the bowl 14. The cotton swab may be made of cotton and have a bulbous-shape which projects outwardly beyond the distal end 64 of the ear cleaning plastic body 12. As stated earlier the use of the cotton swab is optional and some ear cleaning devices may be provided without the cotton swab while others may not be provided with the cotton swab.

In operation, the user will insert the scoop-shaped end or bowl into the ear and gently scrape with the rim, outer top edges 28 of the bowl which are rounded at a radius 38 to allow a general scraping action as the handle is twisted while holding onto the flutes 60 between the fingers. In an embodiment not illustrated, the bowl lacks any openings 24, 35 on the rear surface of the bowl and only the rim edges are used to scrape ear wax and debris. In the illustrated embodiment, a forward or backward axial movement of the device will allow the rear surface of the bowl to use the openings 24 on the underside of the bowl and the backward motion will be able to use the closed slot 35 to collect ear wax. The excess wax and debris will be moved into the openings 24 and into the hollow potion 26 and collected. The user may turn the device and insert the cotton swab end to do cleanup or to apply an ear cleaning solution, if one is desired.

What is claimed is:

1. A disposable ear cleaning device comprising:
   one piece plastic body;
   a handle on the plastic body to be grasped and to be rotated;
   an integral scoop for removing ear wax on the plastic body at one end of the handle;
   the scoop having a bowl portion;
   upper edges on the bowl portion for scraping and collecting wax and for depositing the wax within the bowl portion;
   an outer smooth lower bowl surface on the bowl and a hollow interior in the bowl portion for collecting the wax in the bowl portion and for carrying ear wax deposited therein from the ear;
   an upper front outer edge of the bowl being at a lower height than an upper rear edge of the bowl; and
   a swab of bulbous shape at the other end of the handle for additional cleaning of the ear.

2. An ear cleaning device in accordance with claim 1 wherein a flexible neck portion is provided between the handle and the scoop to bend during use of the device.

3. An ear cleaning device in accordance with claim 2 wherein the neck portion has a reduced cross-sectional thickness.

4. An ear cleaning device in accordance with claim 1 wherein the swab comprises:
   a cotton swab on an end of the handle opposite the bowl portion.

5. An ear cleaning device in accordance with claim 1 wherein the handle has elongated flutes on its outer sides for gripping against rotation of the handle.

6. An ear cleaning device in accordance with claim 1 wherein the ear cleaning device weighs less than one gram.

7. A disposable ear cleaning device comprising:
   an elongated, one piece plastic body having a longitudinal axis;
   a handle on the plastic body to be grasped and to be rotated;
   an integral scoop for removing ear wax on the plastic body attached to the handle;

the scoop having a bowl portion;

upper edges on the bowl portion for scraping and collecting wax and for depositing the wax within the bowl portion;

an outer smooth lower bowl surface on the bowl and a hollow interior in the bowl portion for collecting the wax in the bowl portion and for carrying ear wax deposited therein from the ear;

wherein openings being formed on the lower bowl surface and comprising a pair of parallel slots, and which extend transversely in the lower bowl surface and transversely to the longitudinal axis of the plastic, one-piece body to scrape wax; and a swab of bulbous shape at the other end of the handle for additional cleaning of the ear.

8. An ear cleaning device in accordance with claim 7 comprising:

a cotton swab on an end of the handle opposite the bowl portion.

9. An ear cleaning device in accordance with claim 8 wherein the handle has elongated flutes on its outer sides for gripping against rotation of the handle.

10. An ear cleaning device in accordance with claim 7 wherein the ear cleaning device weighs less than one ounce.

* * * * *